(12) United States Patent
Chisholm et al.

(10) Patent No.: US 9,775,638 B2
(45) Date of Patent: Oct. 3, 2017

(54) BRACED BRACHYTHERAPY NEEDLE

(75) Inventors: Robert F. Chisholm, Highland Park, NJ (US); Jay Reed, Elk Grove Village, IL (US); Kevin Helle, Bartlett, IL (US)

(73) Assignee: MEDI-PHYSICS, INC., Princeton, NJ (US)

( * ) Notice: Subject to any disclaimer, the term of this patent is extended or adjusted under 35 U.S.C. 154(b) by 142 days.

(21) Appl. No.: 13/515,375

(22) PCT Filed: Dec. 22, 2010

(86) PCT No.: PCT/US2010/061764
§ 371 (c)(1),
(2), (4) Date: Jun. 12, 2012

(87) PCT Pub. No.: WO2011/079186
PCT Pub. Date: Jun. 30, 2011

(65) Prior Publication Data
US 2012/0253100 A1    Oct. 4, 2012

Related U.S. Application Data

(60) Provisional application No. 61/289,492, filed on Dec. 23, 2009.

(51) Int. Cl.
*A61N 5/10* (2006.01)
*A61B 17/34* (2006.01)

(52) U.S. Cl.
CPC ........ *A61B 17/3403* (2013.01); *A61N 5/1027* (2013.01); *A61B 2017/3405* (2013.01); *A61N 2005/1012* (2013.01)

(58) Field of Classification Search
CPC ................ A61N 5/1001; A61N 5/1007; A61N 2005/1008; A61N 2005/1009; A61N 2005/1011; A61N 2005/1012; A61M 5/329; A61M 5/3293; A61M 5/34; A61M 5/343; A61M 5/344; A61M 25/06; A61M 25/0612; A61M 25/0625
USPC .......................................................... 600/7, 8
See application file for complete search history.

(56) References Cited

U.S. PATENT DOCUMENTS

| | | | |
|---|---|---|---|
| 4,586,490 A * | 5/1986 | Katz | 600/3 |
| 5,242,373 A | 9/1993 | Scott et al. | |
| 6,059,801 A | 5/2000 | Samimi | |
| 6,159,140 A * | 12/2000 | Loeffler | A61N 5/1002 600/3 |
| 6,235,001 B1 * | 5/2001 | O'Holloran | A61M 37/0069 604/164.07 |
| 6,752,753 B1 * | 6/2004 | Hoskins et al. | 600/7 |
| 2002/0077522 A1 * | 6/2002 | Hamazaki et al. | 600/7 |

(Continued)

FOREIGN PATENT DOCUMENTS

| WO | 9920337 | 4/1999 |
|---|---|---|
| WO | 0128631 | 4/2001 |

OTHER PUBLICATIONS

PCT/US2010/061764 ISRWO Dated Apr. 21, 2011.

*Primary Examiner* — Charles A Marmor, II
*Assistant Examiner* — Thaddeus Cox
(74) *Attorney, Agent, or Firm* — Grogan, Tuccillo & Vanderleeden, LLP (57) ABSTRACT

Braces to reduce bending of a brachytherapy needle during insertion into a patient, as well as methods of using the needle braces and kits useful therefor.

13 Claims, 8 Drawing Sheets

(56) References Cited

U.S. PATENT DOCUMENTS

| | | | |
|---|---|---|---|
| 2003/0028068 A1* | 2/2003 | Steele, Sr. | A61N 5/1007 600/7 |
| 2004/0186340 A1* | 9/2004 | Reed | A61N 5/1027 600/7 |
| 2004/0220444 A1* | 11/2004 | Hogendijk et al. | 600/7 |
| 2006/0063960 A1* | 3/2006 | Wissman | A61N 5/1027 600/7 |
| 2007/0106231 A1* | 5/2007 | Snow | A61M 5/3273 604/263 |
| 2007/0167664 A1* | 7/2007 | Hermann et al. | 600/3 |
| 2007/0219505 A1* | 9/2007 | Zehner | A61M 5/1785 604/198 |
| 2007/0265488 A1* | 11/2007 | Lamoureux | A61M 37/0069 600/7 |
| 2008/0171983 A1* | 7/2008 | Knutson | 604/117 |
| 2010/0016804 A1* | 1/2010 | Muskatello et al. | 604/198 |
| 2011/0201999 A1* | 8/2011 | Cronenberg | A61M 5/2066 604/89 |

* cited by examiner

BRACED BRACHYTHERAPY NEEDLE

This application is a filing under 35 U.S.C. 371 of international application number PCT/US2010/061764, filed Dec. 22, 2010, which claims priority to U.S. application No. 61/289,492 filed Dec. 23, 2009, the entire disclosure of which is hereby incorporated by reference.

FIELD OF THE INVENTION

The present invention is directed to the field of brachytherapy equipment. More specifically, the present invention relates to a brachytherapy needle and a brace to help minimize bending of the needle during needle insertion into a patient.

BACKGROUND OF THE INVENTION

Implanting brachytherapy seeds into a patient typically involves loading a number of such seeds, possibly including spacers between successive and either loosely or within a carrier strand, into a brachytherapy implantation needle. The needles are typically formed from a medically-compliant metal, such as stainless steel. The loaded needle typically includes the seeds at one end within the needle and a stylet extending from the seeds out the opposite end of the needle. A grid, or template, providing guide-holes is sometimes positioned against the patient so that the physician may accurately guide the seeds to their proper location in or about the target tissue by inserting the needle through the proper hole in the grid. The grid body, being about one-inch thick, receives and provides some support to the sharpened end of the needle. The physician typically drives the needle into the patient by grasping the needle by its hub at the free end. It is preferable to hold the needle by the hub so as to reduce the exposure of the hands to the radioactivity of the seeds at the far end. However, as the grid body holds the sharp end of the needle and the physician holds the needle by the hub at the opposite end, dermal resistance to being punctured can lead to buckling stresses on the needle, causing the needle to deflect or bow quite noticeably. Once the needle begins to penetrate the through the dermis into the perineum, the buckling problem dissipates as the inner tissue provides much less resistance than the dermis.

The buckling problem has been more pronounced as the delivery needles get smaller in size. For example, the brachytherapy seeds sold as THINSEED™ (marketed by the General Electric Company through its GE Healthcare business) may be implanted using a 20 gage needle. The buckling problem has been observed in some early procedures using THINSEED. As the needle passageway is typically filled throughout its length by seeds and/or spacers and the stylet, permanent deformation of the needle due to the penetration compression forces applied to it is less likely. Nevertheless, physicians report that the bowing of the needle can be a distraction in performing the operation. Physicians will typically hold the needle body with one hand as the other pushes on the needle hub to drive the needle into the patient. Such a manual technique increases physician exposure to the activity of the loaded needles. While thicker needles could be employed, thinner needles are desirable for the lower insult caused to the patient by the smaller tissue displacement as the needle passes and the thinner seeds remain implanted.

There is therefore a need for a device that will limit the deflection of a brachytherapy needle during penetration. The device should desirably allows the physician to maintain some stand-off from the seeds within the needle so as to help minimize extremity exposure to the activity of the brachytherapy seeds.

SUMMARY OF THE INVENTION

In view of the needs of the prior art, the present invention provides a brachytherapy needle with a brace which reduces bending of the needle as the needle is inserted into a patient.

The present invention also provides a kit for brachytherapy device including at least one brachytherapy needle and a brace for minimizing the bending of the needle as it is inserted into a patient during a brachytherapy implantation procedure.

The present invention also reduces extremity exposure while providing long axis rigidity to the needle to reduce bowing.

In addition to reducing bowing the needle assist can be used as a guide for steering the needle during the penetration process for correct three dimensional placement of the seeds being implanted. This is commonly done by twisting the luer fitting of the needle and repetitively inserting and withdrawing the needle until the desired location is reached. This is also done by guiding the needle by hand, again adding to extremity exposure for the physician.

In addition to eliminating bowing, aiding guidance, and reducing exposure the needle assist can be used to lock the needle stylet to the luer fitting to ensure the materials within the needle are secured during insertion to the patient. This is done by creating a removable resistive material between the needle stylet and the needle luer fitting.

DETAILED DESCRIPTION OF THE PREFERRED EMBODIMENT

The present invention provides braces for brachytherapy needles in order to reduce bowing (or bending or buckling) of the needle due to the longitudinal loads during insertion into a patient. The braces offer convenience to the physicians using the needles by reducing the need to manually hold the needle at a location near the radioactive brachytherapy load during needle insertion. Thus, the braces of the present invention help reduce extremity exposure to the activity of the needle loads by either providing the physician some degree of stand-off from the needle while manipulating it, and/or through the additional shielding the brace provides. Certain of the braces are connected to a stylet lock at the hub of the needle so as to ensure that the brace does not come off of the needle during transportation or handling of the needle prior to implantation.

The braces may be made of suitable materials which provide the structural rigidity to minimize bending of the needles during insertion into a patient. It is further contemplated that the braces may be formed from a material, or materials, which provide additional shielding against the activity of the needle loads while also providing a sufficient grip on the needle to resist movement due to gravitational or inertial forces. It may be desirable for the braces of the present invention to be able to slide along the needle body should the needle to penetrate the patient a distance that is greater than the brace's closest distance to either the patient or the needle grid through which the needle passes proximate to the patient. Certain braces are contemplated to be provided with the brace in position on the needle body, while other braces are to be applied to the needle by the physician prior to implanting the needle. It is further contemplated that any of the braces of the present invention could be provided with a brachytherapy needle in kit form. The needle may be either pre-loaded with a brachytherapy load. The brachytherapy load being either one or more brachytherapy seeds and/or spacers, or a stranded brachtherapy product where one or more seeds and/or spacers are provided in a carrier material or suture as is known in the art.

The operating principle of the present invention is to provide a holding force along the needle body so as to reduce the bowing stress, which is a function of body length. Desirably, the brace is applied generally about the position of maximum bowing (were it to occur), or at a point about mid-way between the needle hub and the placement grid after the needle has been inserted into the grid but prior to penetration of tissue, although the exact placement may be selected by the physician. Once the needle as penetrated the dermis, the bowing forces are generally dissipated as the tissue offers far less resistance to further needle penetration. Thus it is desirable that the brace is able to slide along the needle body should continued insertion of the needle cause the brace to run into the grid body.

Figure 1:
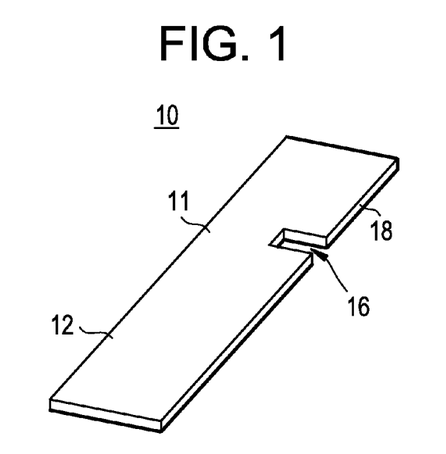
FIG. 1 depicts a first brace of the present invention for a brachytherapy needle.
Figure 2:
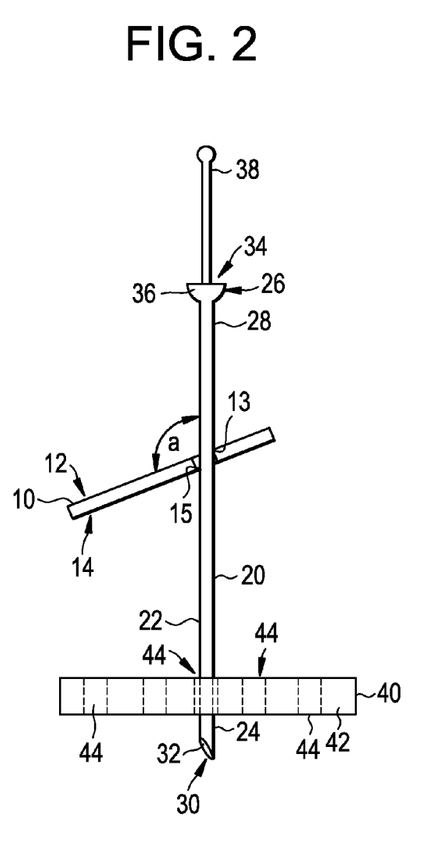
FIG. 2 depicts the brace of FIG. 1 engaging a brachytherapy needle during an implantation procedure.

With reference to FIGS. 1 and 2, the present invention provides a brace 10 for a brachytherapy needle. Brace 10 includes an elongate body 12 having opposed major surfaces 12 and 14. Body 12 defines a notch 16 opening on a perimetrical edge 18 thereof. Notch 16 is defined to include a dimension larger than the cross-sectional width (typically, the diameter) of a brachytherapy needle 20.

Needle 20 is a suitable for performing brachytherapy procedures, such as 16-gage, 18-gage, or 20-gage needle. Needle 20 has a tubular needle body 22 having opposed first and second open ends, 24 and 26 respectively, and an elongate cylindrical body wall 28 extending therebetween. Needle body 22 defines an elongate passageway 30 extending in fluid communication with first and second openings 32 and 34 respectively defined by first and second open ends 24 and 26. Needle 20 includes a brachytherapy load positioned within passageway 30 for dispensing out first end 24, as is known in the prior art. Needle 20 typically includes a needle hub 36 at second end 26 and an elongate stylet 38 which is extendable through opening 34 and passageway 30 for dispensing the brachytherapy load.

With particular reference to FIG. 2, needle 20 is typically inserted through a grid 40 positioned adjacent to a patient. Grid 40 includes a grid body 42 defining a number of parallel passages 44 therethrough in a standardized 2×2 array used for brachytherapy treatment, or dosing, plans. The physician can push on hub 36 to drive first end 24 of needle 20 into the patient towards the target tissue. In order to reduce any bowing, bending, or buckling of needle 20 during needle insertion, the physician may use their free hand to hold brace 10 so that needle body 22 extends generally transversely through notch 16. As the expanse of notch 16 is generally slightly larger than the diameter of needle 20, the physician may thus hold brace 10 at an oblique angle $\alpha$ to needle body 22. Thus, needle body 22 is pinned between opposed notch edges 13 and 15 of opposing major surfaces 12 and 14, respectively. It has been demonstrated that bowing of needle 20 can be reduced or even eliminated by providing a counter-acting holding force along needle body 22. Desirably, brace 10 is positioned at a location about mid-way between hub 36 and grid 40 after needle 20 has been inserted into a passage 44 but prior to penetration of tissue.

Referring now to FIGS. 3A-G, the present invention contemplates that notch 16 of brace 10 may take different forms and be located at different positions than shown in FIG. 1. In each case, the notch is defined to include a dimension larger than the cross-sectional width of said needle body so as to receive the needle body therein such that a tilting of the brace body with respect to the needle body will provide the desired grip to steady the needle body against bowing. Additionally, for FIGS. 3A-G, like numbering will denote like components.

Figure 3A:
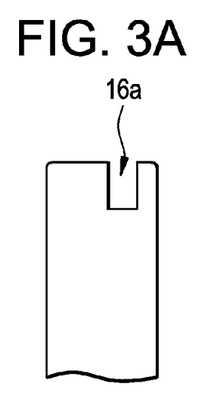
FIGS. 3A-G depict alternative shapes for a notch defined by the brace of FIG. 1.
Figure 3B:
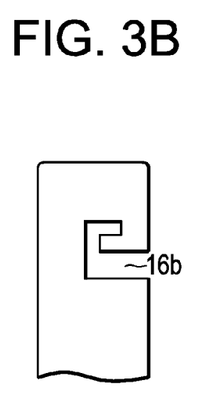
Figure 3C:
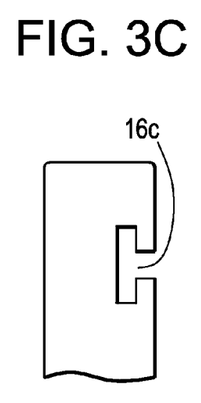
Figure 3D:
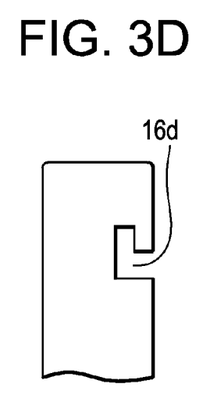
Figure 3E:
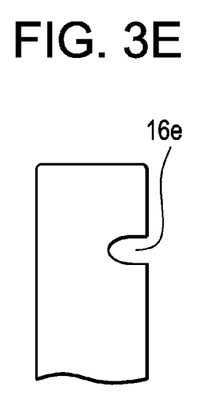
Figure 3F:
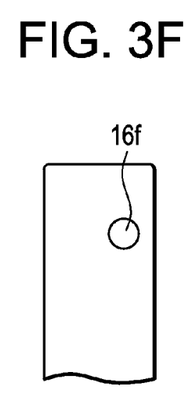
Figure 3G:
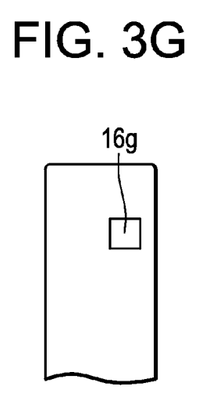

In FIG. 3A, notch 16a is defined at a longitudinal end of brace body 10a. Each of the notches which open on a perimetrical edge of the brace body are contemplated to be located at either a longitudinal end of the brace body or to open transversely with respect to the brace body. In FIG. 3B, notch 16b is defined to have a hook-shape. In FIG. 3C, notch 16c is defined to have a first expanse in fluid communication with a second, larger, expanse. In FIG. 3D, notch 16d is defined to have the shape of a bayonet-connector, or an L-shape. In FIG. 3E, notch 16e is defined by either an arcuate or U-shaped notch edgewall. In FIG. 3F, notch 16F is defined as a bounded arcuate aperture opening on both major surfaces of brace body 12f. In FIG. 3G, notch 16g is defined as bounded rectilinear aperture opening on both major surfaces of brace body 12g.

Figure 4:
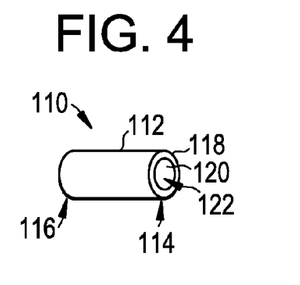
FIG. 4 depicts an alternative brace of the present invention for a brachytherapy needle.
Figure 5:
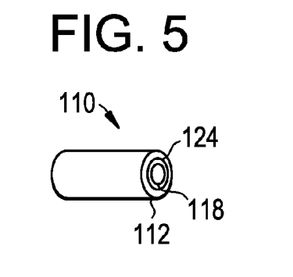
FIG. 5 depicts the brace of FIG. 4 positioned on a brachtherapy needle.
Figure 6:
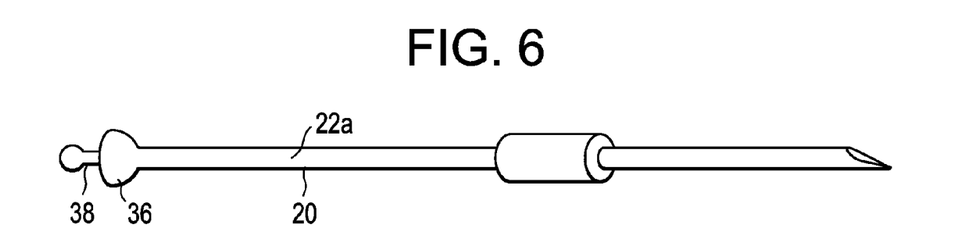
FIG. 6 depicts the brace of FIG. 4 formed as a bi-component device.

FIGS. 4-6 depict a brace 110 of the present invention. Brace 110 includes an elongate cylindrical brace body, or support body, 112 having opposed first and second open ends 114 and 116. Brace body 110 includes a needle engagement member 118. Needle engagement member 118 is an elongate cylindrical wall having an inner surface 120 defining an elongate brace passageway 122 extending in fluid communication between open ends 114 and 116. First end 24 of needle 20 is inserted through brace passageway 122 so that brace 110 is retained on the outer surface 22a thereof. Brace 110 is desirably sized to slideably engage outer surface 22a of needle 20, that is, brace 110 is able to hold its place on needle 20 against gravitational or inertial forces, but is still relatively easy to be slid therealong.

Brace 110 may be formed as a unitary structure, as shown in FIG. 4, or as a two-part structure as shown in FIG. 5. In FIG. 5, engagement member 118 of brace 110 is provided by an inner cylindrical body 124 extending within support body 112. The present invention contemplates that support body 112 is formed from a structurally rigid material to resist the bowing of needle 20 and desirably from a material which attenuates radioactivity or provides additional shielding to a user or technician. Inner cylindrical body 124 is desirably formed from a softer material than support body 112, such as a polymeric material, which can provide some give to needle body on which it is placed.

The longitudinal length of brace 110 may be selected to satisfy the purpose of the present invention, to reduce the bowing of its respective needle. For example, while brace 110 may be from about 0.25 inches to 1 inch in length, the present invention contemplates that the length is only limited by the length of needle extending between the needle hub and the grid body when the needle has reached its maximum insertion depth. The thickness of brace 10 is selected to be sufficient for the needle on which it is to be positioned. It is further contemplated that brace body 112 forms one or more detents or projections which may be deflected to engage the needle body onto which it has been positioned.

Figure 7:
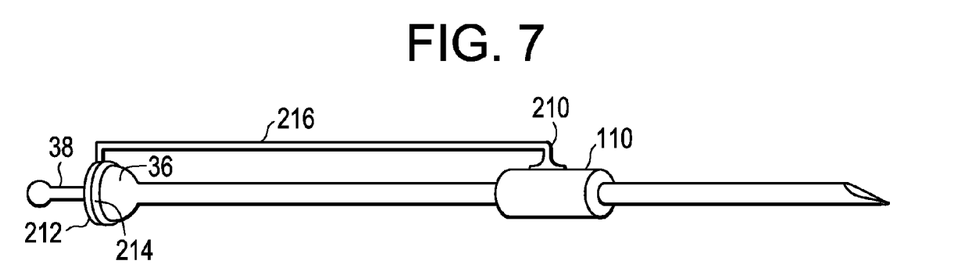
FIG. 7 depicts another brace of the present invention for a brachytherapy device positioned on a brachytherapy needle.

FIG. 7 depicts brace 210 having a brace body 112 (as described for FIGS. 4-6) affixed to a stylet lock 212. Stylet lock 212 includes an annular rim 214 through which stylet 38 extends locking engagement and a spacing arm 216 which holds brace body 112 a fixed distance from hub 36 of needle 20. Spacing arm 216 is selected to be a length which still allows needle 20 to be inserted to the required dispense depth within the patient. Stylet lock engages hub 36 and stylet 38 and holds stylet 38 in place against gravitational and inertial forces but still allows the physician to advance stylet 38 within the needle passageway to effect dispensing of the brachytherapy load.

Figure 8:
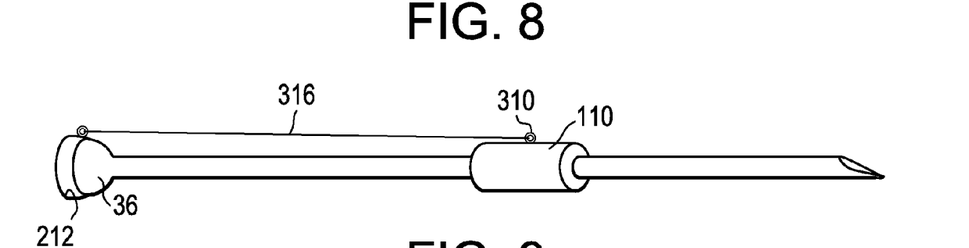
FIG. 8 depicts yet another brace of the present invention positioned on a brachytherapy needle.

FIG. 8 depicts brace 310 having a brace 110 (as described for FIGS. 4-6) affixed to a stylet lock 212 (as described for FIG. 7). Brace 310 includes a deflectable spacing arm 316 which limits the maximum spacing of brace body 110 from hub 36 of needle 20, while allowing brace body 110 to be urged towards hub 36.

Figure 9:
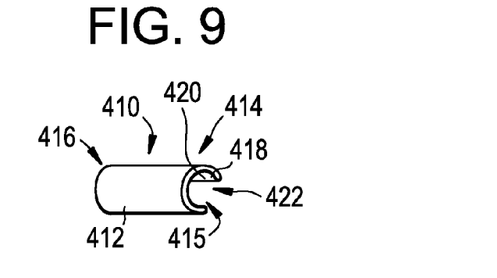
FIG. 9 depicts still another brace of the present invention.

FIG. 9 depicts a brace 410 of the present invention. Brace 410 includes an elongate cylindrical brace body, or support body, 412 having opposed first and second open ends 414 and 416. Brace body 412 also defines an elongate transversely-opening channel 415 along the length thereof. Brace body 410 includes a needle engagement member 418. Needle engagement member 418 is an elongate cylindrical wall having an inner surface 420 defining an elongate brace passageway 422 extending in fluid communication between open ends 414 and 416. First end 24 of needle 20 is inserted through brace passageway 422 so that brace 410 is retained on the outer surface 22a thereof. Alternatively, should brace body be formed of a sufficiently flexible material, the present invention contemplates that needle 20 may be inserted through channel 415 into passageway 422. Brace 410 is desirably sized to slideably engage outer surface 22a of needle 20, that is, brace 410 is able to hold its place on needle 20 against gravitational or inertial forces, but is still relatively easy to be slid therealong. The present invention contemplates that brace 410 extends sufficiently about needle 20 to prevent needle 20 from bowing back through channel 415. The present invention also contemplates that multiple braces 410 may be applied to a single needle, in which case it would be desirable to arrange the channels 415 of each brace to extend in different orientations about needle 20.

Figure 10:
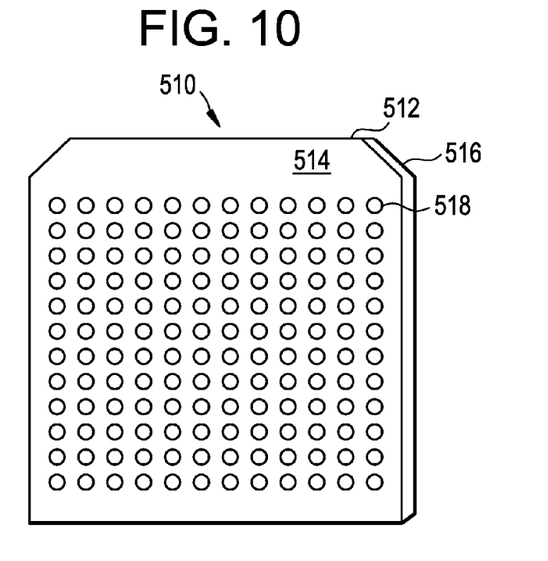
FIG. 10 depicts still yet another brace of the present invention.
Figure 11:
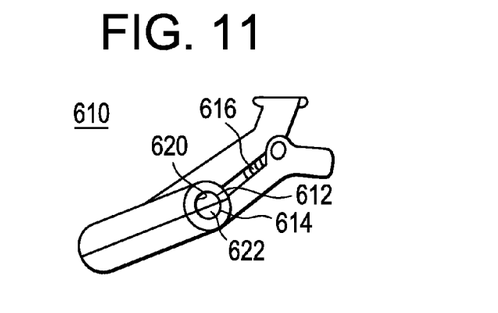
FIG. 11 depicts even yet another brace of the present invention.
Figure 12:
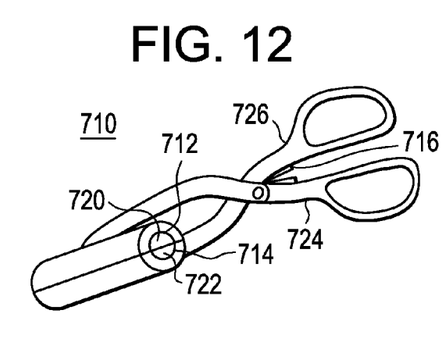
FIG. 12 depicts even still yet another brace of the present invention.
Figure 13:
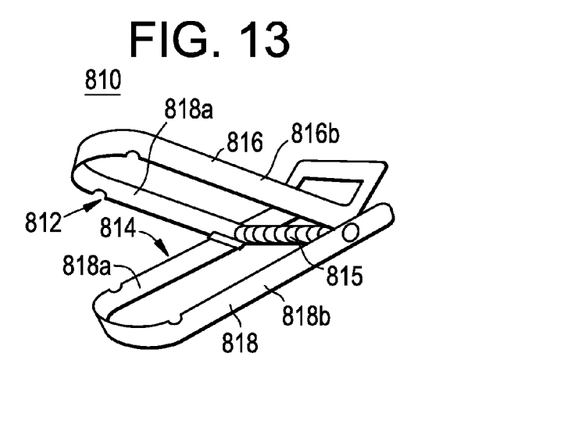
FIG. 13 depicts even still yet another brace of the present invention.

FIG. 10 depicts a brace 510 of the present invention. Brace 510 includes a planar body 512 having opposed major faces 514 and 516. Body 512 defines a number of passages 518 extending in parallel therethrough, arranged in a 2×2 matrix array corresponding to a brachytherapy dose plan, to open on faces 514 and 516. The present invention contemplates that brace 510 may have more than a single needle extending therethrough, desirably each needle loaded and positioned in accordance with the dose plan. As only a single needle will be dispensed at a time, brace 510 may be held by the physician at a location from the dispensing needle that reduces any bowing of that needle during needle penetration into a patient. Brace 510 may be shipped with a carrier kit for a dose plan as is more fully described in copending patent application, filed on even date herewith, the entire contents of which are hereby incorporated by reference as if fully disclosed herein FIGS. 11-13 depict various clamp braces of the present invention. The clamp braces of the present invention provide spring-loaded clamps for holding a portion of a brachytherapy needle at multiple points therealong so as to minimize deflection of the needle during insertion into a patient. The clamps of the present invention are contemplated as either grasping the surface of the needle at distinct points or along a length of the surface thereof. The clamp braces include opposing first and second surfaces which are urgeable towards each other by a resilient spring means for engaging the tubular body of said needle. A physician opens the clamp brace by overcoming the spring means to urge the opposed surfaces away from each other so that the needle body may be inserted therebetween. The physician then relaxes the opening force to allow the opposing surfaces to close about the needle body. It is contemplated that a single clamp brace may be use for each of the needles provided for a single dose plan, although each needle may alternatively be provided with its own clip.

In FIG. 11, clamp brace 610 includes opposing first and second surfaces 612 and 614 which are urgeable towards each other by a resilient spring means 616 for engaging the tubular body of needle 20. Desirably, one or both of first and second surfaces 612 and 614 defines an elongate arcuate channel 620 and 622 which conform about needle body 22 to thereby provide support fully thereabout. It is contemplated that arcuate channels 620 and 622 are sized to allow clamp brace 610 to grasp and hold onto needle 20 without slippage due to gravitational or inertial forces.

In FIG. 12 clamp brace 710 includes opposing first and second surfaces 712 and 714 which are urgeable towards each other by a resilient spring means 716 for engaging the tubular body of needle 20. Desirably, one or both of first and second surfaces 712 and 714 defines an elongate arcuate channel 720 and 722. Arcuate channels 720 and 722 thus provide a semi-cylindrical wall which together conform about needle body 22 to thereby provide support thereabout. It is contemplated that arcuate channels 720 and 722 are sized to allow clamp brace 710 to grasp and hold onto needle 20 without slippage due to gravitational or inertial forces. Clamp brace 710 further includes an elongate first arm 724 supporting first surface 712 at one end thereof and an elongate second arm 726 supporting second surface 714 at one thereof. First and second arms are pivotally connected so as to allow movement of first surface 712 towards and away from second surface 714.

In FIG. 13, clamp brace 810 includes a support member having opposing first and second surfaces 812 and 814 which are urgeable towards each other by a resilient spring means 815 for engaging the tubular body of needle 20. First and second surfaces 812 and 814 are provided as opposing surfaces of opposed U-shaped walls 816 and 818. It is further contemplated that either U-shaped wall 816 or 818 may be instead provided by a pair of transversely-spaced elongate arms 816a, 816b or 818a, 818b, respectively. Clamp brace 810 thus provide two pairs of spaced hold points for needle 20.

Figure 14:
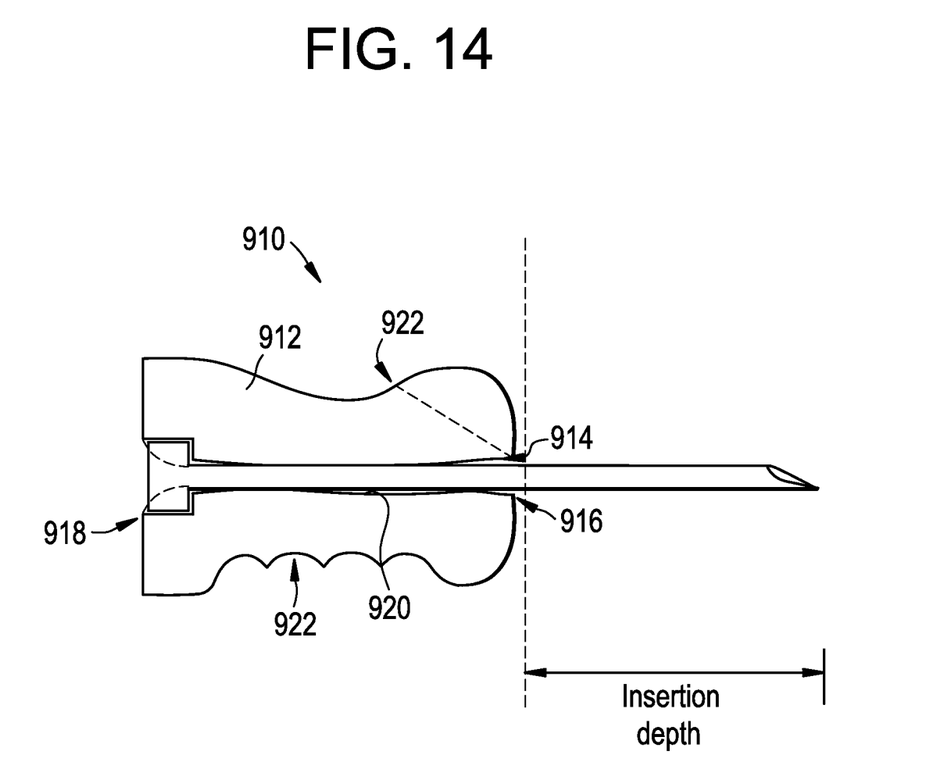
FIG. 14 depicts even still yet another brace of the present invention.

FIG. 14 depicts another brace 910 of the present invention. Brace 910 includes a brace body 912 and includes an elongate cylindrical inner surface 914 which defines opposed apertures 916 and 918 and an elongate needle passage 920 extending in fluid communication therebetween. Brace body 912 includes an outer surface 922 shaped to ergonomically conform to a user's hand or fingers. The length of body 912 is desirably limited to allow needle 20 to be inserted to a desired depth within a patient. It is contemplated that brace 910 may be preferably used in procedures where a physician desires to grip about needle 20. As such, brace body 912 is desirably formed from a radiation-shielding material so as to further protect the extremity gripping brace 910.

Figure 19:
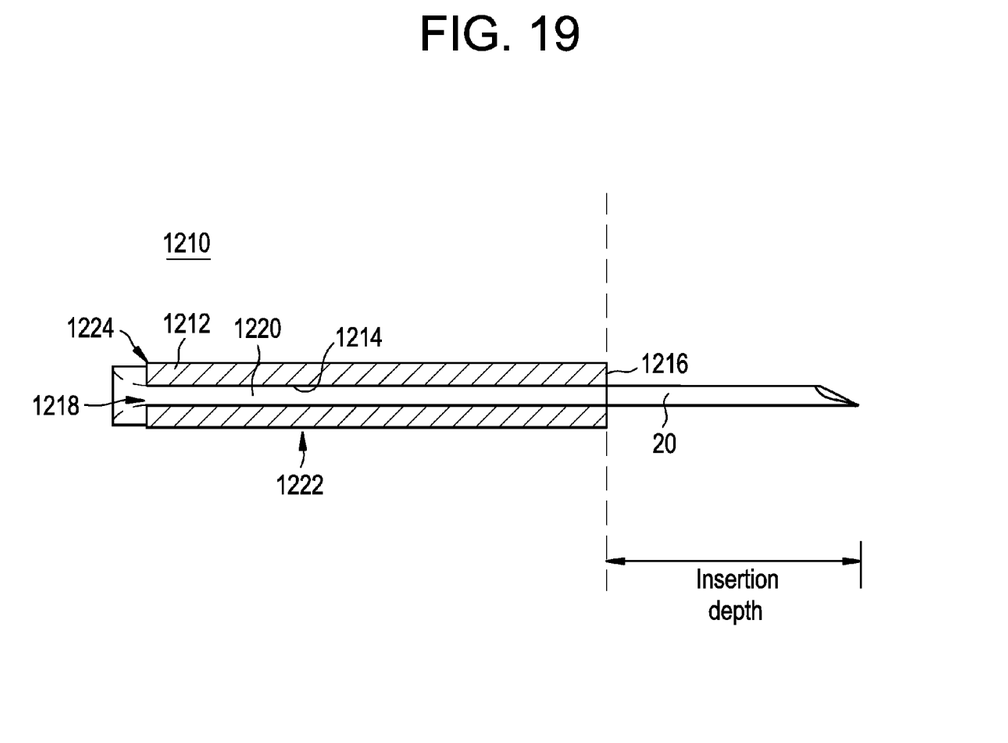
FIG. 19 depicts yet still another brace of the present invention.

FIG. 19 depicts another brace 1210 of the present invention. Brace 1210 includes an elongate cylindrical brace body 912 having an elongate cylindrical surface 1214 defining opposed apertures 1216 and 1218 and an elongate needle passage 1220 extending in fluid communication therebetween. Brace body 1212 includes an elongate cylindrical outer surface 1222. The length of body 1212 is desirably limited to allow needle 20 to be inserted to a desired depth within the patient. Brace body further includes a hub-engaging surface 1224 for limiting insertion of needle 20 through passage 1220. Brace body 1212 is desirably formed from a radiation-shielding material although may be formed of a suitable metal or rigid plastic.

Figure 15:
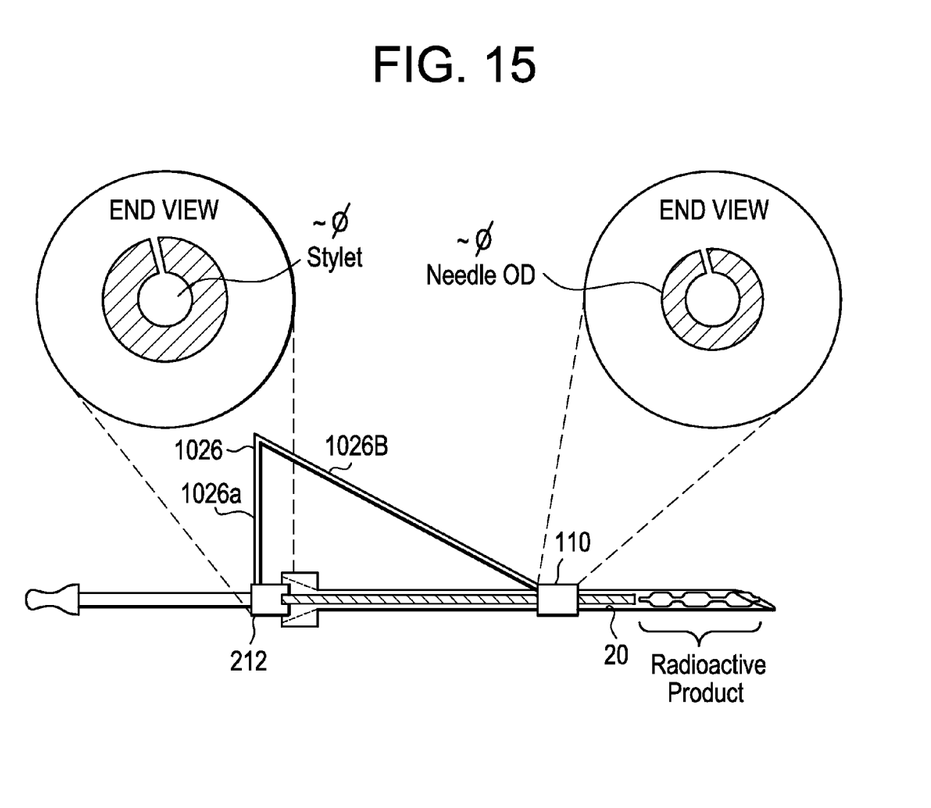
FIG. 15 depicts still yet even another brace of the present invention.

FIG. 15 depicts another brace 1010 of the present invention. Brace 1010 is similar in concept to braces 210 in that a brace body 110 is connected to a stylet lock 212 by a two-segment spacing arm 1126. Spacing arm 1026 includes a first segment 1026a extending from lock 212 substantially normal to needle 20 and a second segment 1026b connected between brace body 112 and first segment 1026a. Spacing arm 1026 thus provides a transverse stand-off from the brachytherapy load within needle 20 where a physician may hold brace 1010 at a lower risk of exposure. The present invention further contemplates that the brace 410 may be incorporated into this design as well.

Figure 16:
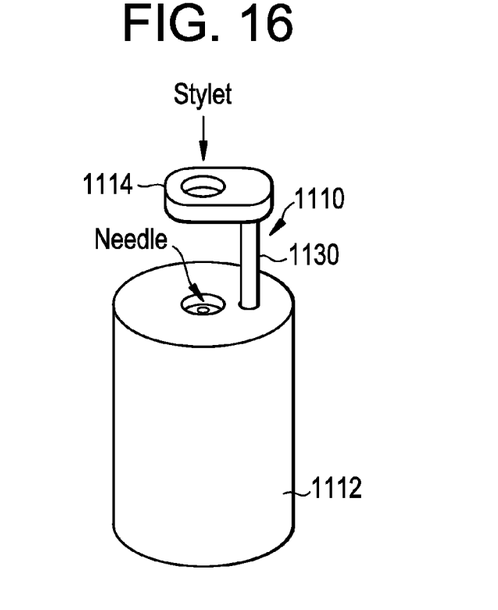
FIGS. 16-18 depicts even still another brace of the present invention.
Figure 17:
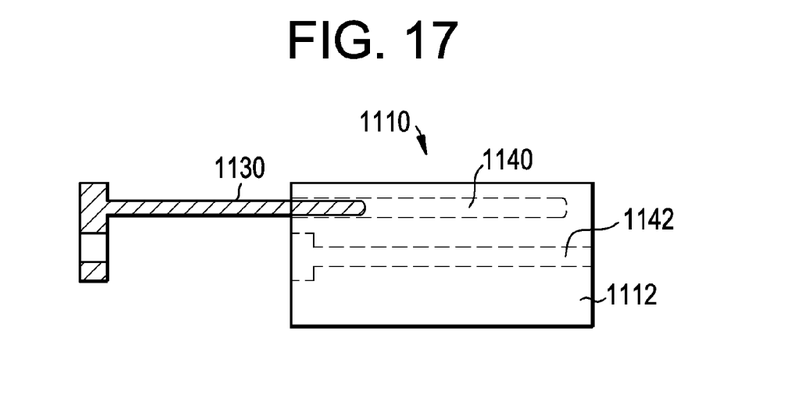
Figure 18:
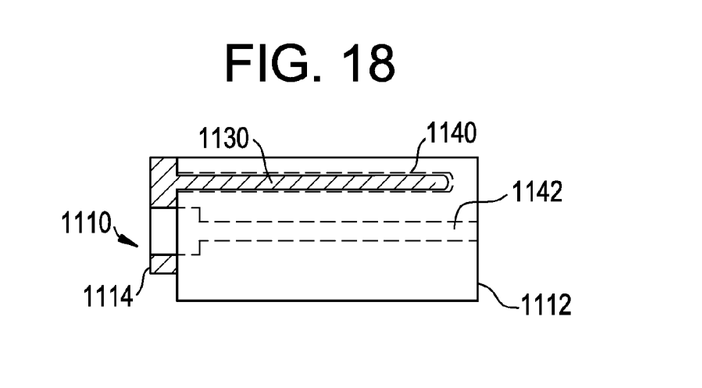

FIGS. 16-18 depict brace 1110 of the present invention. Brace 1110 is similar in concept to brace 310 in that a brace body 1112 is urgeable towards a stylet lock 1114 located at the needle hub. Brace 1110 includes bushing rod 1130 which is receivable within a bushing passageway 1132 defined by the brace body 1112. The loaded needle is inserted through the aperture in stylet lock 1114 and then through passageway 1142 defined through brace body 1112. The needle hub will abuttingly engage stylet lock 1114 as it is too large to pass through its aperture. The needle hub will travel towards brace body 1112, and thus be inserted into a patient out the opposite end of body 1112, with stylet lock 1114 as bushing rod 1130 extends into bushing passage 1140. The bulk of brace body 1112 will counter the deflection of the needle body as it is inserted into the patient.

The present invention further provides a kit for a brachytherapy procedure, the kit includes an elongate needle having a tubular needle body and a brace of the present invention adapted to engage a portion of said body wall of said needle so as to reduce bending of said needle as said needle is inserted into a patient. The needle desirably includes at least one brachytherapy source positioned within said passageway thereof. The kit desirably also includes an elongate stylet adapted to be extendable through the needle so as to effect dispensing of the brachytherapy source. The kit is desirably provided sterilized within a sealed container which maintains the sterility of the kit components.

While the particular embodiment of the present invention has been shown and described, it will be obvious to those skilled in the art that changes and modifications may be made without departing from the teachings of the invention. The matter set forth in the foregoing description and accompanying drawings is offered by way of illustration only and not as a limitation. The actual scope of the invention is intended to be defined in the following claims when viewed in their proper perspective based on the prior art.

What is claimed is:

1. A brachytherapy device comprising:
   an elongate needle having a tubular needle body, said tubular needle body comprising opposed first and second open ends and an elongate cylindrical body wall extending therebetween, said body wall having an inner surface defining an elongate passageway extending in fluid communication with first and second openings respectively defined by said first and second open ends, and an outer surface, said second open end of said tubular body defining a needle hub; and
   at least one brachytherapy source positioned within said passageway of said needle; and
   a brace for said needle which engages a portion of said outer surface of said body wall of said needle intermediate said first open end and said needle hub so as to reduce bending of said needle as said needle is inserted into a patient, wherein said brace comprises an elongate cylindrical support body and an inner cylindrical body received within the elongate cylindrical support body, said inner cylindrical body having an inner surface and defining an engagement member that is adapted to slidably receive said outer surface of said body wall of said needle intermediate said first open end and said needle hub, wherein said brace provides shielding from radioactivity and wherein said inner cylindrical body defining said engagement member is a softer material than said support body to provide a degree of give to said needle body over which said brace is received.

2. The brachytherapy device of claim 1, wherein said inner surface of said inner cylindrical body defining said engagement member comprises at least one projection configured to be deflected to engage said needle body.

3. The brachytherapy device of claim 1, wherein said engagement member is formed from a different material than said outer cylindrical body.

4. The brachytherapy device of claim 1, wherein said support body includes a length and further defines an elongate transverse opening along the length of said support body.

5. The brachytherapy device of claim 1, wherein said brace further includes a hub-engaging member, wherein said support body is connected to said hub-engaging member.

6. The brachytherapy device of claim 1, further comprising:
- an elongate stylet received through said needle hub and in said elongate passageway of said needle; and
- a stylet lock engaged with said needle hub, said stylet lock being configured to hold said stylet in place within said elongate passageway of said needle;
- wherein said stylet lock includes a spacing arm extending from a distal end of said needle hub to said brace.

7. The brachytherapy device of claim 6, wherein said spacing arm is deflectable and is configured to limit a maximum spacing of said brace from said hub of said needle while allowing said brace to be urged toward said hub.

8. A brachytherapy brace for a brachytherapy needle having an elongate tubular body having opposed first and second open ends, said brachytherapy brace comprising an elongate rigid cylindrical support body and an inner cylindrical body received within the support body, said inner cylindrical body defining an engagement member having an inner surface and being adapted to slidably engage said tubular body of said needle intermediate said opposed first and second open ends so as to reduce bending of said needle as said needle is inserted into a patient, wherein said brace provides shielding from radioactivity, and wherein said inner cylindrical body defining said engagement member is a softer material than said support body to provide a degree of give to said tubular body of said needle over which said brace is placed.

9. A kit for a brachytherapy procedure, said kit comprising:
- an elongate needle having a tubular needle body, said tubular needle body comprising opposed first and second open ends and an elongate cylindrical body wall extending therebetween, said body wall having an inner surface defining an elongate passageway extending in fluid communication with first and second openings respectively defined by said first and second open ends, and an outer surface, and
- at least one brachytherapy source positioned within said passageway of said needle; and
- a brace adapted to engage a portion of said outer surface of said body wall of said needle intermediate said opposed first and second open ends so as to reduce bending of said needle as said needle is inserted into a patient, wherein said brace comprises an elongate rigid cylindrical support body and an inner cylindrical body received within the cylindrical support body, said inner cylindrical body having an inner surface and defining an engagement member that is adapted to slidably receive said outer surface of said body wall of said needle intermediate said first and second open ends of said needle body, wherein said brace provides shielding from radioactivity, and wherein said inner cylindrical body defining said engagement member is a softer material than said support body to provide a degree of give to said needle body over which said brace is placed.

10. The kit of claim 9, wherein said engagement member is formed from a different material than said outer cylindrical body.

11. The kit of claim 9, wherein said support body further defines an elongate transverse opening along the length of said support body.

12. The kit of claim 9, further comprising:
- an elongate stylet received through said second open end of said tubular needle body and in said elongate passageway of said needle; and
- a stylet lock engaged with said needle second open end of said tubular needle body, said stylet lock being configured to hold said stylet in place within said elongate passageway of said needle;
- wherein said stylet lock includes a spacing arm extending from said second open end of said tubular needle body to said brace.

13. A brace for a brachytherapy needle having an elongated tubular body, the brace comprising:
- an elongated cylindrical support body;
- an inner cylindrical body received within the elongated cylindrical support body, said inner cylindrical body defining an engagement member having an inner surface configured to slidably receive an outer surface of a portion of the tubular body intermediate opposed first and second open ends of said tubular body;
- wherein said inner cylindrical body is formed from a softer material than the support body to provide a degree of give to said tubular body of said needle over which said brace is received; and
- wherein the brace provides shielding from radioactivity; and
- wherein the first open end of the tubular body is configured to be inserted into a patient, and the second open end includes a hub.

* * * * *